United States Patent [19]

Nishimoto et al.

[11] Patent Number: 4,884,449
[45] Date of Patent: Dec. 5, 1989

[54] APPARATUS FOR DETECTING A FAILURE IN BEARINGS

[75] Inventors: Shigeto Nishimoto; Yoshiki Fujimoto, both of Osaka; Noriaki Inoue, Sohja; Shunji Harada, Ashiya, all of Japan

[73] Assignees: Koyo Seiko Co., Ltd, Osaka; Kawasaki Steel Corporation, Hyogo, both of Japan

[21] Appl. No.: 201,968

[22] Filed: Jun. 3, 1988

[30] Foreign Application Priority Data

| Jun. 3, 1987 | [JP] | Japan | 62-140481 |
| Jun. 3, 1987 | [JP] | Japan | 62-140482 |
| Jun. 3, 1987 | [JP] | Japan | 62-140484 |
| Jun. 3, 1987 | [JP] | Japan | 62-140485 |
| Jun. 3, 1987 | [JP] | Japan | 62-140486 |

[51] Int. Cl.⁴ .................................. G01N 29/04
[52] U.S. Cl. ............................... 73/660; 73/587
[58] Field of Search ............... 73/587, 593, 660, 602

[56] References Cited

U.S. PATENT DOCUMENTS

| 3,924,456 | 12/1975 | Vahaviolos | 73/587 |
| 4,024,522 | 5/1977 | Clark et al. | 73/587 |
| 4,481,819 | 11/1984 | Yoneyama et al. | 73/593 |
| 4,574,633 | 3/1986 | Ohnuki et al. | 73/587 |
| 4,609,994 | 9/1986 | Bassim et al. | 73/587 |
| 4,738,137 | 4/1988 | Sugg et al. | 73/587 |

FOREIGN PATENT DOCUMENTS 61-198057 9/1986 Japan ........................ 73/593

Primary Examiner—Stewart J. Levy
Assistant Examiner—Louis M. Arana
Attorney, Agent, or Firm—Wenderoth, Lind & Ponack

[57] ABSTRACT

An apparatus for detecting a failure in a bearing has an acoustic emission sensor which detects acoustic emission from the bearing and outputs signals indicative of power of the acoustic emission, a bandpass filter which passes only signals in the range of from 100 kHz to 500 kHz out of the signals received from the aforementioned sensor, and a comparator which compares each of the signals in the range of from 100 kHz to 500 kHz extracted by the bandpass filter with a predetermined threshold value and outputs event signals each of which expresses that the signal from the bandpass filter exceeds the threshold value. This apparatus also has a computer which receives the event signals from the comparator, determines time intervals in which the event signals occur, totals the number of event signals for respective timer intervals, and determines whether or not the number of totaled events exceeds a predetermined threshold value to determine a failure in the bearing.

5 Claims, 16 Drawing Sheets

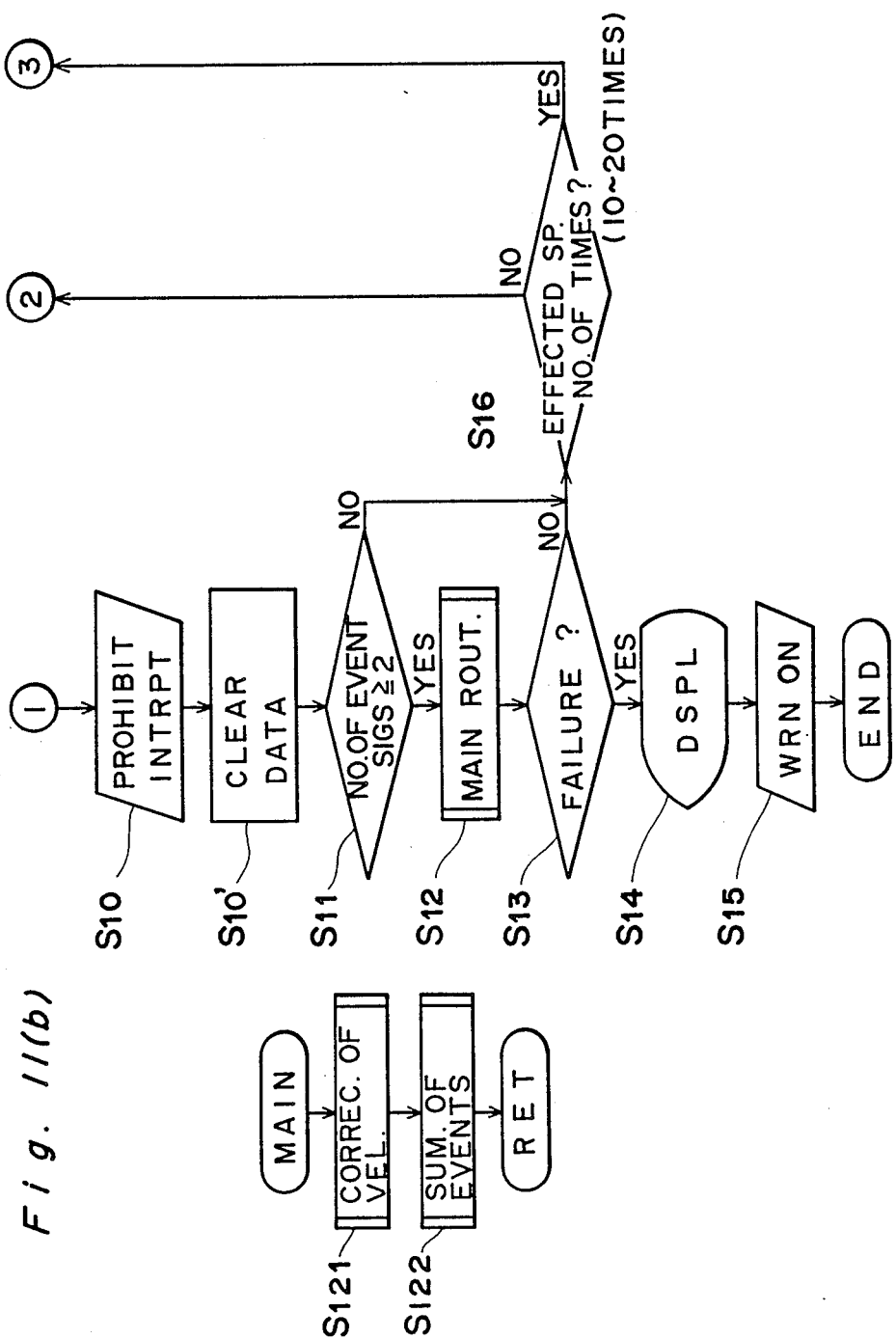

APPARATUS FOR DETECTING A FAILURE IN BEARINGS

BACKGROUND OF THE INVENTION

The present invention relates to an apparatus for detecting a failure in bearings, and particularly to an apparatus which uses acoustic emission (hereinafter referred to as AE).

Devices such as the following have conventionally been used as bearing failure detection apparatuses for detecting bearing failure by detecting acoustic emission. This bearing failure detection apparatus detects AE signals from bearings using an AE sensor, compares the output of the AE sensor in a comparator with a threshold value, and judges a bearing abnormality when the AE signal exceeds the aforementioned threshold value. Furthermore, the number of events in which the AE signal level exceeds a given threshold level is counted, and a bearing failure is judged by whether the sum of these events exceeds a given threshold value.

However, because the aforementioned conventional bearing failure detection apparatus judges bearing failure by simply determining whether the AE signal level exceeds a given threshold level, there has been a problem of erroneous bearing failure detection in factories in which are installed rolling mills which produce strong AE signals at the metal-in time (i.e. - the time when the rolling of a metal sheet is started or the time when the metal sheet is loaded into the mill) and at other times because strong AE signals from sources other than the bearings cannot be discriminated from the AE signal from the bearing themselves.

SUMMARY OF THE INVENTION

Accordingly, a first object of the present invention is to provide an apparatus for detecting a failure in a bearing apparatus which can minimize the effects of background noise and detect initial flaking of bearings.

A second object of the present invention is to provide an apparatus for detecting a failure in a bearing which can accurately detect bearing abnormalities through the processing of the AE signal even in an environment in which acoustic emission is generated by elements other than bearings or in an environment in which there is strong external noise.

A third object of the present invention is to provide an apparatus for detecting a failure in ball-and-roller bearings for rolling machines which can accurately detect bearing abnormalities without erroneous bearing failure judgements by stopping bearing failure evaluation at the metal-in time and the metal-out time the metal-out time being that time at which the end part of a metal sheet passes out of the mill.

A fourth object of the present invention is to provide an apparatus for detecting a failure in ball-and-roller bearings for rolling machines which can accurately detect bearing failure with an evaluation period of only two to three turns of the bearing without such ball-and-roller bearing failure evaluation being executed in real-time, and moreover, which can efficiently and accurately detect bearing failure with multiple bearings. Even though an AE signal is received and a failure in an ball-and-roller bearing is detected during the rolling period excluding a predetermined period after the reception of a rolling signal (metal-in signal) and a period prior to the reception of a rolling signal (metal-out signal), the reception period of the AE signal is from 4 to 15 seconds, and the ball-and-roller bearing may not turn two to three revolutions. Thus, the problem remains that bearing failure may not be accurately detected using the AE signal. The fourth object of the present invention is to resolve this problem.

A fifth object of the present invention is to provide a method of detecting a failure in a bearing which enables accurately setting of the AE signal threshold value or level independent of worker intuition or actual machinery breakage, and which can therefore accurately detect bearing failure, and moreover, can automatically set the threshold level.

In order to achieve the aforementioned first object, an apparatus for detecting a failure in a bearing according to the present invention comprises:

an acoustic emission sensor which detects acoustic emission from the bearing and outputs signals indicative of power of the acoustic emission;

a bandpass filter which passes only signals those signals received from the aforementioned sensor in the range of from 100 kHz to 500 kHz; and a comparison means for comparing each of the signals in the range of from 100 kHz to 500 kHz extracted by the bandpass filter with a predetermined threshold value and for outputting an event signal when the signal from the bandpass filter exceeds the threshold value.

In order to achieve the aforementioned second object, an apparatus for detecting a failure in a bearing according to the present invention comprises:

an acoustic emission sensor which detects acoustic emission from the bearing and outputs signals indicative of power of the acoustic emission; the acoustic emission being related to the failure of the bearing a bandpass filter which passes only those signals received from the aforementioned sensor in the range of from 100 kHz to 500 kHz;

a comparison means for comparing each of the signals in the range of from 100 kHz to 500 kHz extracted by the bandpass filter with a predetermined threshold value and for outputting an event signal when the signal from the bandpass filter exceeds the threshold value;

a period determination means for receiving the event signals from the comparison means and for determining the time intervals in which the event signals occur the time intervals being related to the portion of the bearing suffering a failure;

a totalizing means for totaling the number of event signals for respective time intervals determined by the period determination means; and a judging means for judging whether or not the number of events totalized by the totalizing means exceeds a predetermined threshold value to judge a bearing failure.

A brief description of the operation of the above-mentioned apparatus is as follows.

Acoustic emissions from a bearing and other sites are detected by the AE sensor, which outputs AE signals. Of the AE signals outputted from the AE sensor, signals from 100 kHz to 500 kHz are extracted by the bandpass filter, each of the output signals from this bandpass filter is compared by the comparison means with a specified threshold value, and if said output signal exceeds the aforementioned threshold value, an event signal expressing such a condition or event is outputted. The period determination means receives event signals from the comparison means and determines time intervals in which the event signals occur. The totalizing means calculates the total number of events at each time interval. The number of events for each interval totalized by the totalizing means is compared with a predetermined threshold value by the judging means, and a bearing failure is judged when the number of events for the interval exceeds the threshold value. Furthermore, which element of the bearing is suffering from a failure is judged according to the interval for which the number of events exceeds the threshold level.

In order to achieve the aforementioned third object, an apparatus for detecting a failure in ball-and-roller bearings for rolling mills according to the present invention compriser:

a comparison means for comparing an acoustic emission signal indicative of power of an acoustic emission from ball-and-roller bearings with a predetermined threshold value, and for outputting an error signal which expresses a bearing failure when the power of the acoustic emission exceeds the predetermined threshold value; and a logic circuit for invalidating the output of the comparison means for a specified interval of time during a metal-in time when a metal sheet is loaded into the rolling mill or when the rolling of the metal sheet is started and during a metal-out time when an end of the metal sheet passes out of the mill.

A brief description of the operation of the above-mentioned apparatus is as follows.

The logic circuit invalidates signals outputted from the comparison means for a specified time during the metal-in and metal-out time in response to a rolling signal. Thus, the judgement of failures in the bearings through the judgement of the AE signals is stopped during the metal-in and metal-out times, and accordingly accurate bearing failure judgement with ball-and-roller bearings in rolling mills becomes possible.

In order to achieve the aforementioned fourth object, a method of detecting a failure in ball-and-roller bearings for a rolling mill is characterized by the steps of:

extracting by means of a bandpass filter signals in the range of from 100 kHz to 500 kHz out of signals inputted from an acoustic emission sensor which detects acoustic emission from a bearing;

comparing by means of a comparison means each of the signals extracted and outputted by the bandpass filter with a predetermined threshold value;

storing in a memory an event, which is generated during rolling except for a given period of time after reception of a metal-in signal and a given period of time before reception of a metal-out signal, when the output of the bandpass filter exceeds the threshold value;

repeating the above steps of extracting, comparing, and storing a specified number of times for each of a multiple number of bearings; and finally detecting bearing failure based on the number of events stored in the memory.

A brief description of the operation of this method is as follows.

Events are detected for specified number of times for each of a multiple number of bearings, each event being when the output signal of the bandpass filter exceeds the threshold value during rolling except for a given time duration after the metal-in and a given time duration or period before the metal-out. In this way, such measurements of acoustic emission for each one of the multiple number of bearings are repeated a specified number of times during except for the given time duration after reception of the metal-in signal and the given time duration before reception of the metal-out signal, and therefore, bearing failure is accurately detected even for an extremely short measurement time not including the given time duration after the metal-in and the given time duration before the metal-out.

In order to achieve the aforementioned fifth object, a method of detecting a failure in a bearing to be executed by a machine having an acoustic emission sensor which detects acoustic emission from a bearing, a bandpass filter which extracts signals in the range of from 100 kHz to 500 kHz from signals outputted of the acoustic emission sensor, a comparison means which compares each of the signals outputted from the bandpass filter with a threshold value, thereby detecting a failure in the bearing based upon a result of the comparison, is characterized by the steps of:

BRIEF DESCRIPTION OF THE DRAWINGS

The present invention will become more fully understood from the detailed description given hereinafter and the accompanying drawings which are given by way of illustration only, and thus are not limitative of the present invention, and wherein:

FIGS. 13 (*b*), (*c*), and (*d*) each are graphs showing the distribution of the number of events of AE signals during each period;

DETAILED DESCRIPTION OF PREFERRED EMBODIMENTS (First embodiment)

A first embodiment of the present invention is described below with reference to FIGS. 1 to 3.

Figure 2:
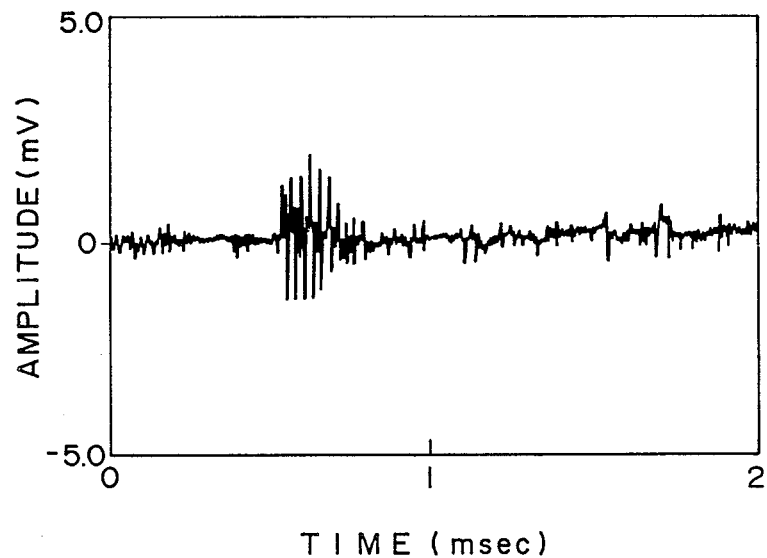
FIG. 2 is a waveform diagram of an AE signal.
Figure 3:
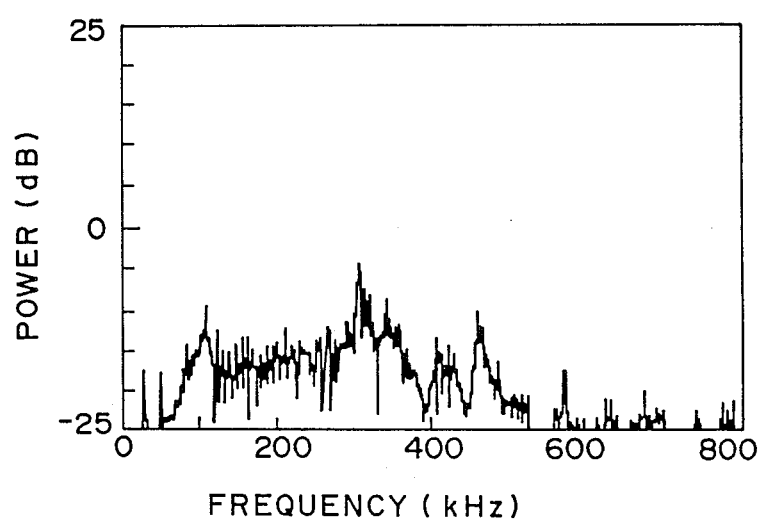
FIG. 3 is a graph showing the power spectrum of the AE signal.

The inventors of the present invention have discovered that when initial flaking of a bearing occurs, an AE signal is generated from this initial flaking, and the waveform and spectrum of this AE signal are as shown in FIGS. 2 and 3. Since these waveform and spectrum are characterized by a frequency range of from 100 kHz to 500 kHz, initial flaking of the bearing can be detected by detecting signals in the range from 100 kHz to 500 kHz as shown in FIG. 3.

An apparatus for detecting a failure in a bearing according to this first embodiment of the present invention is based on the aforementioned discovery and characterized by the provision of an acoustic emission sensor 1 which detects acoustic emission from the bearing and outputs signals indicative of power of the acoustic emission;

- a bandpass filter 3 which passes only signals in the range of from 100 kHz to 500 kHz out of the signals received from the aforementioned sensor 1; and
- a comparison means 6 which compares each of the signals in the range of from 100 kHz to 500 kHz extracted by the bandpass filter 3 with a predetermined threshold value and outputs event signals each of which expresses that the signal from the bandpass filter 3 exceeds the threshold value.

Figure 1:
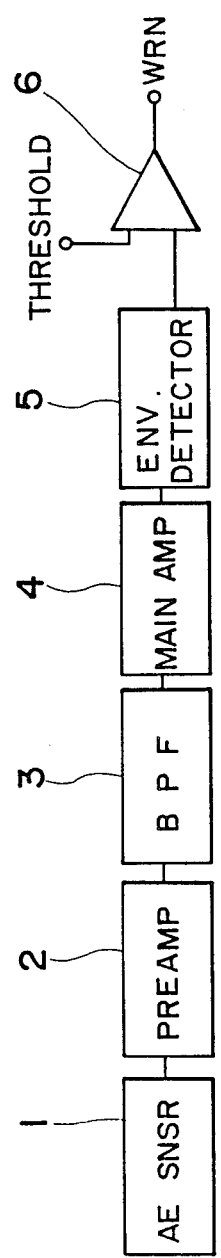
FIG. 1 is a block diagram of a bearing failure detection apparatus according to a first embodiment of the present invention.

In FIG. 1, reference number 1 is an AE sensor; element 2 is a preamplifier; element 3 is a bandpass filter which passes an AE signal in the range of from 100 kHz to 500 kHz and preferably from 200 kHz to 500 kHz; element 4 is a main amplifier; element 5 is a envelope detector, and element 6 is a comparator which functions as a determination means, comparing an output of an AE signal after envelope detection by the envelope detector 5 with a theshold value, and determining initial flaking of a bearing when the aforementioned AE signal exceeds the threshold level, and issuing a warning in response thereto.

According to the above construction, an AE signal from the bearing (not shown in the figures) is detected by AE sensor 1. This AE signal is waveshaped in a manner such as shown in FIG. 2, passes preamplifier 2 and is inputted to bandpass filter 3 from which only a frequency band within the range of from 100 kHz to 500 kHz, which has a correlation to the occurrence of initial flaking of the bearing as shown in FIG. 3, is extracted. The output from said bandpass filter 3 is further amplified by main amplifier 4, and inputted to comparator 6 immediately after envelope detection by envelope detector 5. The envelope detected signal from envelope detector 5 is compared with a threshold value by comparator 6; when this envelope detected signal has a higher level than the reference value, initial flaking of the bearing is determined and a warning is issued.

In this manner, initial flaking of the bearing can be accurately judged without being influenced by low frequency background noise of less than several ten kilohertz because only AE signals with a frequency in the range of 100–500 kHz which has a correlation to initial flaking is extracted from the AE signals emitted from the bearing.

As will be clear from the above description, a bearing failure detection apparatus according to the present invention can accurately judge initial flaking of a bearing without being influenced by background noise because such apparatus is provided with a sensor which detects acoustic emission from the bearing, a bandpass filter which passes an output in the range of between 100 kHz and 500 kHz from the output of the aforementioned sensor, and a judging means which compares the output of from 100 kHz to 500 kHz extracted from the aforementioned bandpass filter with a reference value, and determines initial flaking of the bearing.

(Second embodiment)

Figure 4:
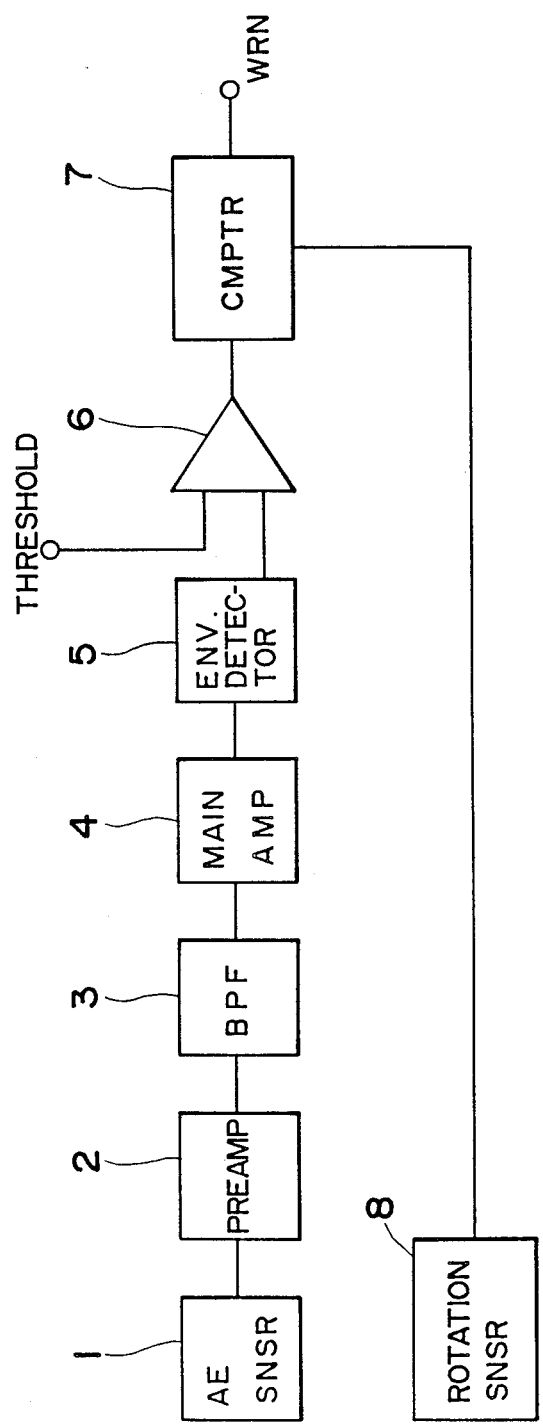
FIG. 4 is a block diagram of a bearing failure detection apparatus according to a second embodiment of the present invention.
Figure 5A:
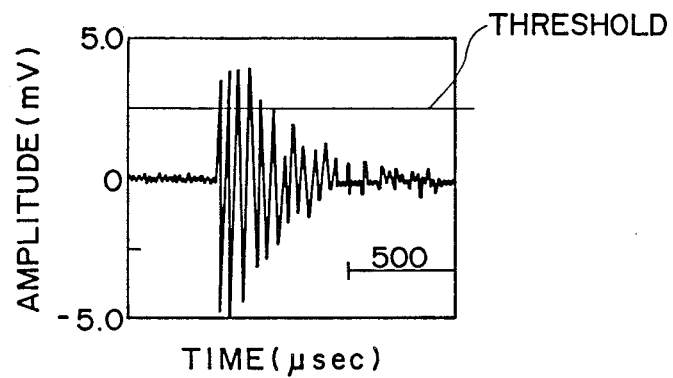
FIGS. 5 (*a*), (*b*), (*c*), (*d*), and (*e*) are figures showing the waveform and number of events at each part according to this embodiment, FIGS. 5(*d*) and (*e*) being schematically illustrated.
Figure 5B:
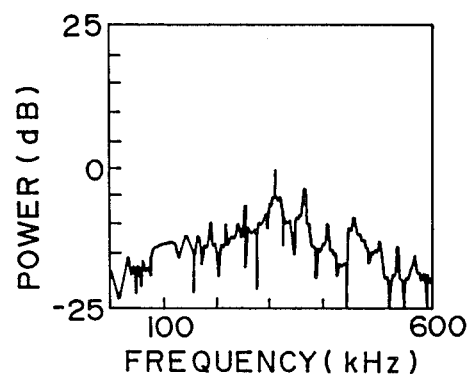
Figure 5C:
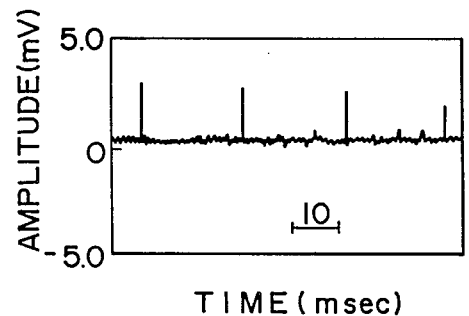
Figure 5D:
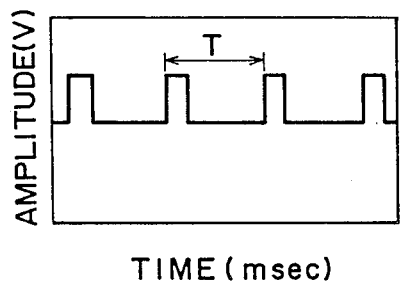
Figure 5E:
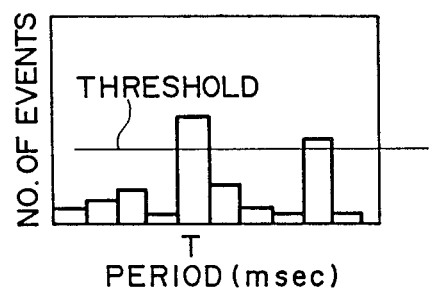
Figure 6:
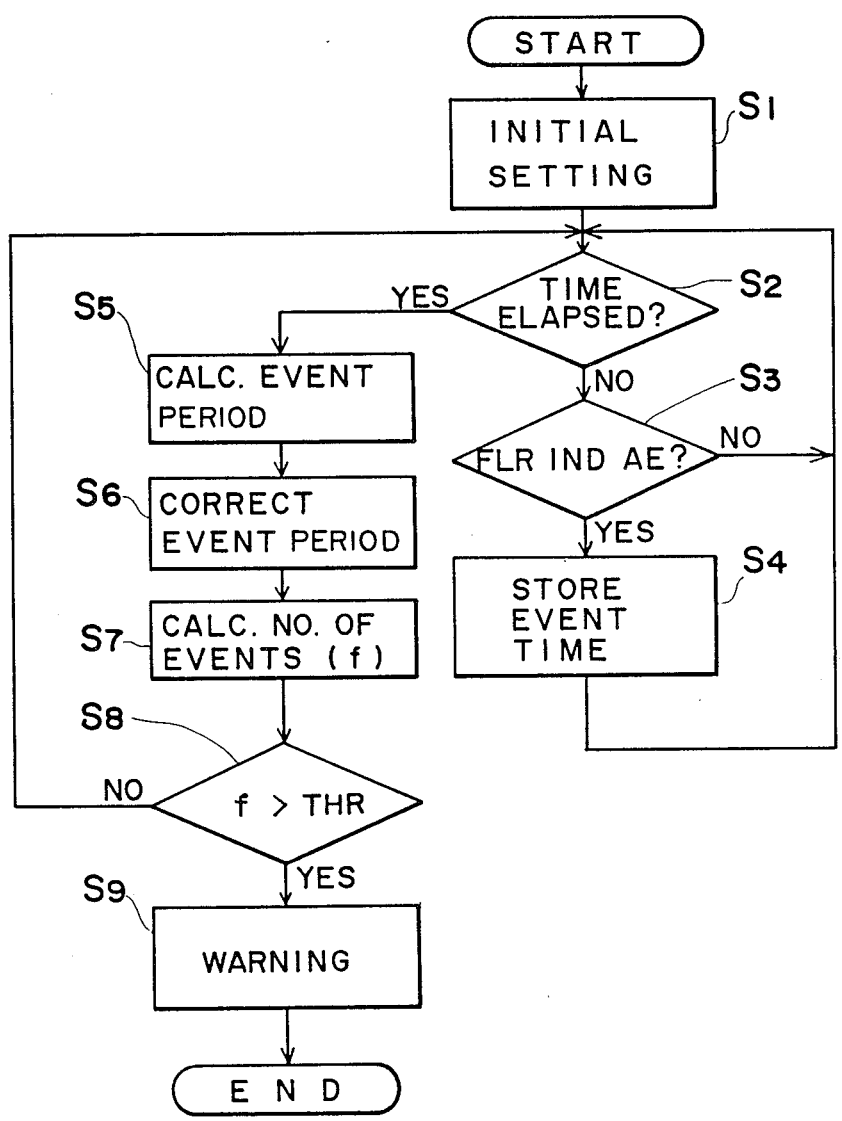
FIG. 6 is a flow chart of the aforementioned embodiment.

A second embodiment of the present invention is described herein with reference to FIGS. 4 to 6.

A bearing failure detection apparatus according to a second embodiment of the present invention is characterized by the provision of an acoustic emission sensor 1 which detects acoustic emission from the bearing and outputs signals indicative of power of the acoustic emission;

- a bandpass filter 3 which passes only signals in the range of from 100 kHz to 500 kHz out of the signals received from the aforementioned sensor 1;
- a comparison means 6 which compares each of the signals in the range of from 100 kHz to 500 kHz extracted by the bandpass filter 3 with a predetermined threshold value and outputs event signals each of which expresses that the signal from the bandpass filter 3 exceeds the threshold value;
- a period determination means which receives the event signals from the comparison means and determines periods of time in which the event signals occur;
- a totalizing means which totals the number of event signals for respective periods of time calculated by the period calculation means; and
- a judging means which determines a bearing failure by determining whether or not the number of events totaled by the totalizing means exceeds a predetermined threshold value.

In FIG. 4, reference number 1 is an AE sensor which detects acoustic emission from a bearing. AE signals which express the strength of the acoustic emission and are outputted from AE sensor 1 are amplified by preamplifier 2, are inputted to bandpass filter 3 through which AE signals in the range of from 100 kHz to 500 kHz, and preferably from 200 kHz to 500 kHz, pass, and noise is removed. The AE signal from which noise has been removed by aforementioned bandpass filter 3 is further amplified by main amplifier 4, inputted to envelope detector 5, and envelope detected. An AE signal has a waveform such as, for example, shown in FIG. 5 (a), and a spectrum such as shown in FIG. 5 (b). The waveform after envelope detection by envelope detector 5 becomes such as is shown in FIG. 5(c). The AE signal after envelope detection is compared with a constant threshold value by comparator 6, and when said AE signal exceeds the level of the threshold value, a pulse such as shown in FIG. 5 (d) is outputted to computer 7. Furthermore, the number of revolutions of the bearing per unit time is inputted to computer 7 from a rotation sensor 8.

Processing such as shown in FIG. 6 is applied in the aforementioned computer 7.

First, an initial setting is made at step S1 in FIG. 6, the procedure advances to step S2, and determination is made as to whether a previously defined specified time has elapsed. If at this stage it is determined that the specified time has not elapsed, step S3 is advanced to where the reception of a pulse from comparator 6 determines whether acoustic emissions indicating the failure of the bearing have been generated; if it is determined that acoustic emissions have not been generated, step S2 is returned to; if it is determined that acoustic emissions have been generated, step S4 is advanced to and the time of event at which this acoustic emission was detected is stored in memory, and step S2 is returned to. After repeating these steps S2, S3, and S4, if it is determined at step S2 that the specified time has elapsed, step S5 is advanced to, and each period at which AE signal level exceeds the threshold value is calculated using the event time stored at step S4. Next, step S6 is advanced to, and, based on the change in the number of revolutions per unit time of the bearing received from rotation sensor 8 during the passage of the specified period of time with respect to a reference number of revolutions, each period calculated at step S5 is corrected to a period per reference number of revolutions. Specifically, each period calculated at step S5 is multiplied by the number of revolutions per unit time of the bearing detected by rotation sensor 8, and divided by the reference number of revolutions. Next, step S7 is advanced to and the number (F) of AE signals for respective periods are summed up. Specifically, as shown in FIG. 5 (e), the number of occurrences of events for respective period or frequency of AE signal's exceeding the threshold is calculated. Next step S8 is advanced to where it is determined whether or not the frequency of acoustic emissions per any event cycle exceeds a given threshold level THR as shown in FIG. 5 (e); when the number of events "f" exceeds the threshold level, bearing damage is determined, step S9 is advanced to and a warning expressing bearing failure is outputted. Step S2 is returned to if at step S8 it is determined that the number of events "f" does not exceed the threshold level THR.

Furthermore, it is possible to judge the site of bearing damage based on the period at which the number of events exceeds the threshold level. Specifically, if the aforementioned bearing is a roller bearing in which the inner ring is a rotating ring, and the frequency at which a roller passes a given single site on the inner ring is designated Fi, the rotational frequency of the shaft is Fr, the frequency at which the roller passes a specified site on the outer ring is Fo, the rotational frequency of the roller is Fb, and the rotational frequency of the cage is Fc, then acoustic emission will be generated at the following period:

1/Fi, 1/Fr when the failure is on the inner ring,
1/Fo when the failure is on the outer ring, and
1/Fb, 1/Fc when the failure is on the roller.
(T in FIGS. 5 (d) and (e) represents any one of the above periods.)

Specifically, the event period of the acoustic emission differs according to which of the inner ring, outer ring, and roller has a damage. Therefore, it is possible to judge whether flaking has occurred at the inner ring, outer ring, or roller according to the event cycle or period at which the number of events exceeds the threshold level.

This embodiment can accurately detect failures such as flaking occurring in the bearing, and furthermore can specify the flaking site in the bearing because AE signals greater than a given amplitude are detected after removal of noise by a bandpass filter with a bandwidth of 100 kHz to 500 kHz, the number of events that such AE signals greater than a given value are detected are accumulated by respective periods, and a bearing failure is judged when this accumulated number exceeds a predetermined specified value at a specified period. Furthermore, while changes in the number of revolutions of the bearing affect the event period of the acoustic emission, the damage site of the bearing can be accurately specified without being influenced by variations in the bearing speed because the number of revolutions from the rotation sensor is detected to compensate the event period. Furthermore, because bearing failure is judged using the accumulated value of AE signals generated in a specified cycle or period, bearing failure can be accurately detected in environments in which acoustic emissions from sources other than bearings are generated, such as when metal is loaded in a rolling mill, and in the presence of other large external noises.

In the aforementioned preferred embodiment according to the present invention, the threshold level with which acoustic emission amplitude is compared is a constant value, but the threshold level may be varied according to the level of external noise. Furthermore, in the aforementioned preferred embodiment, the acoustic emission event cycle or period is compensated after completion of a specified time, but the acoustic emission event cycle may be compensated with each acoustic emission. Moreover, in cases in which the number of revolutions of a bearing is constant or changes in the number of revolutions are expected, the constant number of revolution and the expected number of revolutions may be inputted to computer 7 for the compensation of acoustic emission event cycle or period without using rotation sensor 8. In the case in which the number of revolution of a bearing is constant and judging the damage site of a bearing is not required, it is also possible to not compensate the acoustic emission event cycle.

As will be clear from the above description, bearing failure can be accurately detected by a bearing failure detection apparatus according to the present invention even in environments in which acoustic emissions from sources other than bearings are generated, and in large external noise environments because the apparatus is provided with a comparison means which compares an AE signal from an AE sensor with a specified threshold value, a period calculation means which calculates different periods at which events that AE signals exceed the threshold value occur, a totalizing means which totalizes the number of events for respective different periods, and a judging means which judges whether the number of events totalized by the totalizing means exceeds another specified threshold level, whereby the apparatus accumulates the number of events at each event period, and judges a bearing failure when such accumulated value exceeds the threshold value.

Furthermore, a bearing failure detection apparatus according to the present invention can handle variations in period and can accurately specify the damage site of the bearing even in cases in which the number of revolutions of a bearing changes because a signal expressing the number of revolutions of the bearing is received from a rotation sensor, and the event period calculated by the period calculation means is compensated by a period compensation means to an event period of a reference number of revolutions of the bearing.

(Third embodiment)

A third embodiment of the present invention is described below with reference to FIGS. 7 to 9.

An apparatus for detecting a failure in ball-and-roller bearings for rolling mills according to this preferred embodiment of the present invention is characterized by a comparison means 11 which compares an acoustic emission signal indicative of power of an acoustic emission from ball-and-roller bearings with a predetermined threshold value, and outputs an error signal which expresses a bearing failure when the power of the acoustic emission exceeds the predetermined threshold value; and a logic circuit (14) which invalidates the output of the comparison means for a specified time during the metal-in time and the metal-out time based on rolling signals.

Figure 9:
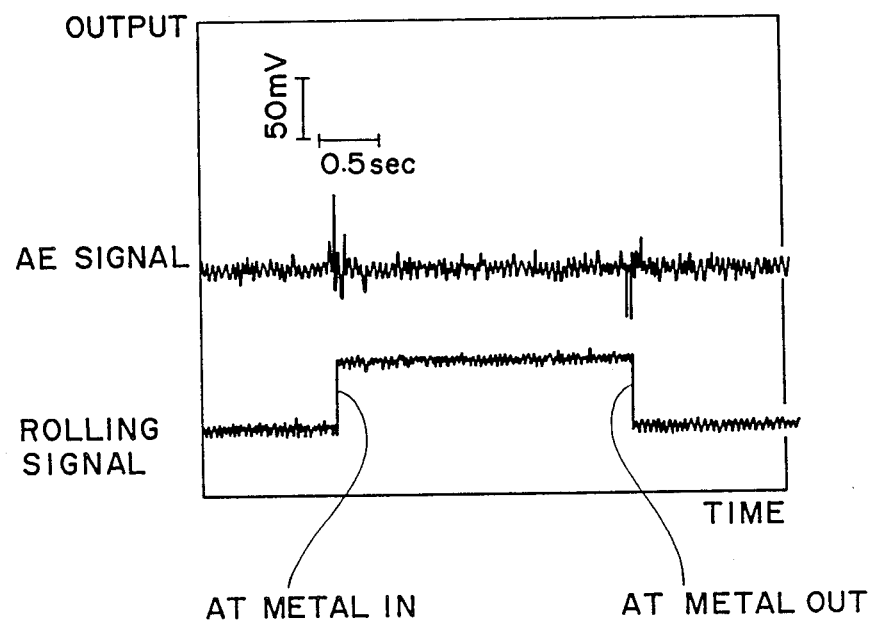
FIG. 9 is a graph showing the waveform of an AE signal and a rolling signal.

In a rolling mill, as shown in FIG. 9, even if a large AE signal is emitted during metal-in and metal-out times this AE signal produced during metal-in and metal-out times is removed by logic circuit 14, and an erroneous false judgement when the bearing is good does not occur.

Figure 7:
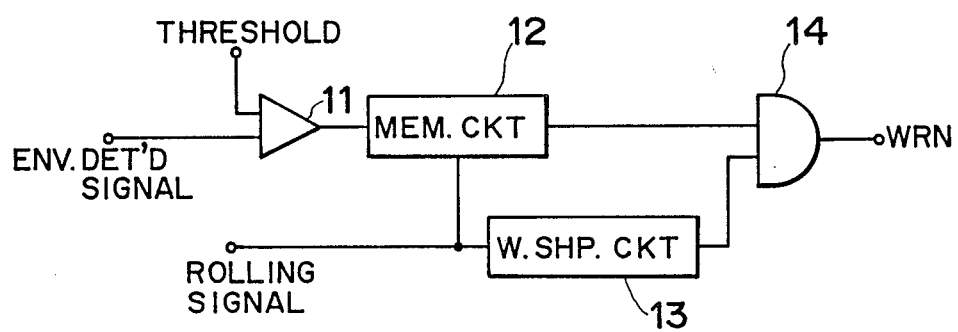
FIG. 7 is a block diagram of a ball-and-roller bearing failure detection apparatus according to a third embodiment of the present invention.
Figure 8:
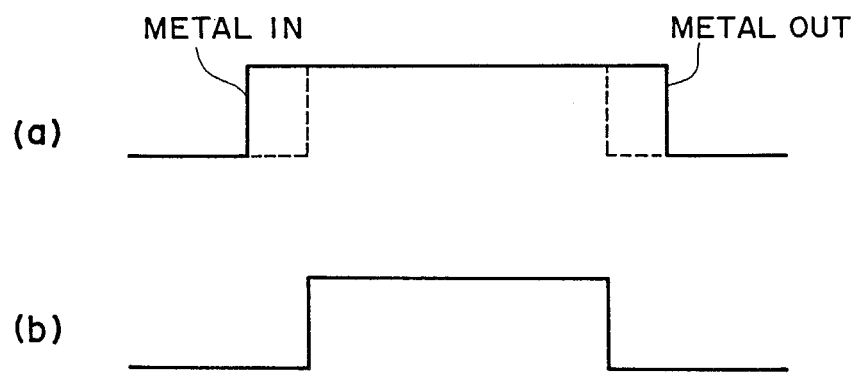
FIG. 8 is a graph showing a rolling signal and a waveshaped signal.

Though an AE sensor, an amplifier, a bandpass filter and an envelope detector are not shown in FIG. 7, these are used in this embodiment as in the second embodiment of FIG. 4. An AE signal outputted from the AE sensor is amplified by the amplifier, a signal within a specified range passes the bandpass filter and is envelope detected by the envelope detector, and the envelope detected signal is inputted to comparator 11 shown in FIG. 7. The envelope detected signal is compared with a threshold value by said comparator 11, and a high level signal is outputted to memory circuit 12 when the envelope detected signal exceeds the threshold or reference value. Moreover, a rolling signal such as shown in FIG. 8 (a) is inputted to said memory circuit 12 and to waveform shaping circuit 13. The aforementioned memory circuit 12 receives this rolling signal, and after metal-in, specifically during rolling, successively stores the output of comparator 11. The aforementioned wave shaping circuit 13 cuts off the rolling signal for a specified time after metal-in and for a specified time before metal-out, and waveshapes the signal as shown in FIG. 8 (b). AND circuit 14 which is a logic circuit receives the output from said memory circuit 12 and from said wave shaping circuit 13, ANDing the waveform shown in FIG. 8 (b) and the output from memory circuit 12, and outputs a high level signal and issues a warning when both the output of memory circuit 12 and the output of waveform shaping circuit 13 occur.

In this way, this bearing failure detection apparatus obtains a signal from comparator 11 to memory circuit 12 only during rolling, does not record the output from comparator 11 during non-rolling, and can save memory capacity. Furthermore, because the bearing load during non-rolling is low and acoustic emissions due to bearing failure are extremely weak even if emitted, since the signal-to-noise ratio deteriorates in such a case, the output of comparator 11 is obtained to memory circuit 12 only during rolling, thus improving the signal-to-noise ratio.

Furthermore, because in this way AND circuit 14 invalidates the output of comparator 11 during the specified time after metal-in and before metal-out, erroneous judging of bearing failure does not occur even when a large AE signal is emitted from the rolling mill during metal-in and metal-out as shown in FIG. 9.

In the aforementioned preferred embodiment, AND circuit 14 is used as the logic circuit, and the output of the comparator is invalidated for a given time after metal-in and before metal-out after, but input to comparator 11 of the envelope detected signal may be stopped for a specified time after metal-in and before metal-out by, for example, providing an AND circuit before comparator 11. Furthermore, the warning signal output from said AND circuit 14 may be received, the cycle of the warning signals calculated, and bearing failure may be judged by judging whether the number of warning signals totalized at respective different cycles exceeds a threshold level.

As will be clear from the above description, a bearing failure detection apparatus according to the present invention can disregard AE signals occurring at metal-in and metal-out in bearing failure judging, and can accurately judge ball-and-roller bearing failure without errors during rolling mill operation because a comparison means which compares an AE signal from an AE sensor with a reference or threshold value, and a logic circuit which invalidates the output of said comparison means for a constant time at metal-in and metal-out based on a rolling signal are provided.

Furthermore, because if the output of the comparison means is made valid only during rolling by the logic circuit, there is no judging of bearing errors during non-rolling times, deteriorations in the signal-to-noise ratio are prevented, and efficient bearing failure judging can be accomplished.

(Fourth embodiment)

A fourth embodiment of the present invention is described below with reference to FIGS. 10 and 11.

A method of detecting a failure in ball-and-roller bearings for rolling mills according to the embodiment of the present invention is characterized by the steps of:

extracting by means of a bandpass filter signals in the range of from 100 kHz to 500 kHz out of signals inputted from an acoustic emission sensor which detects acoustic emission from a bearing;

comparing by means of a comparison means each of the signals extracted and outputted by the bandpass filter with a predetermined threshold value;

storing in memory an event, which is generated during rolling except for given periods of time after reception of a metal-in signal and before reception of a metal-out signal, when the output of the bandpass filter exceeds the threshold value;

repeating the above steps of extracting, comparing, and storing a specified number of times for each of a multiple number of bearings; and finally detecting bearing failure based on the number of events stored in the memory.

Figure 10:
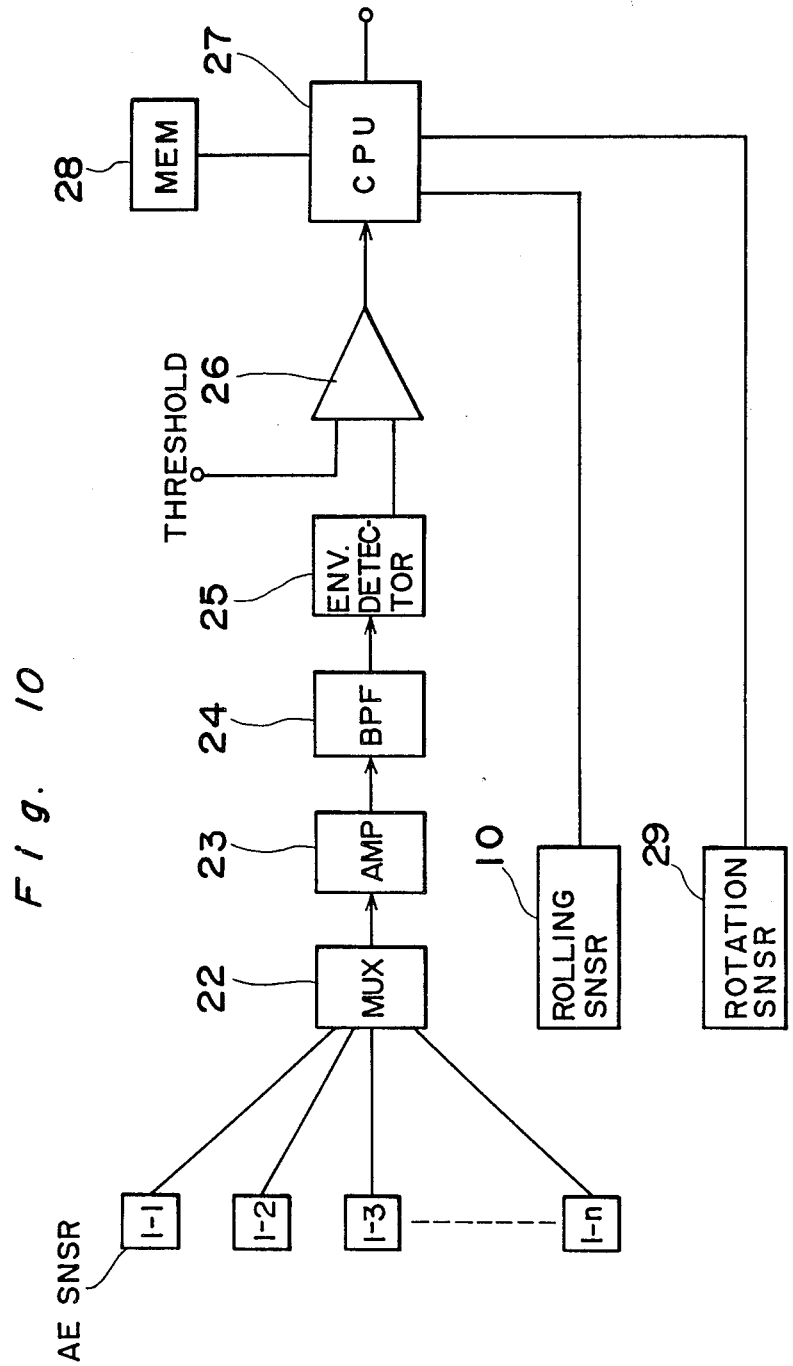
FIG. 10 is a block diagram of a fourth embodiment of the present invention.
Figure 11A:
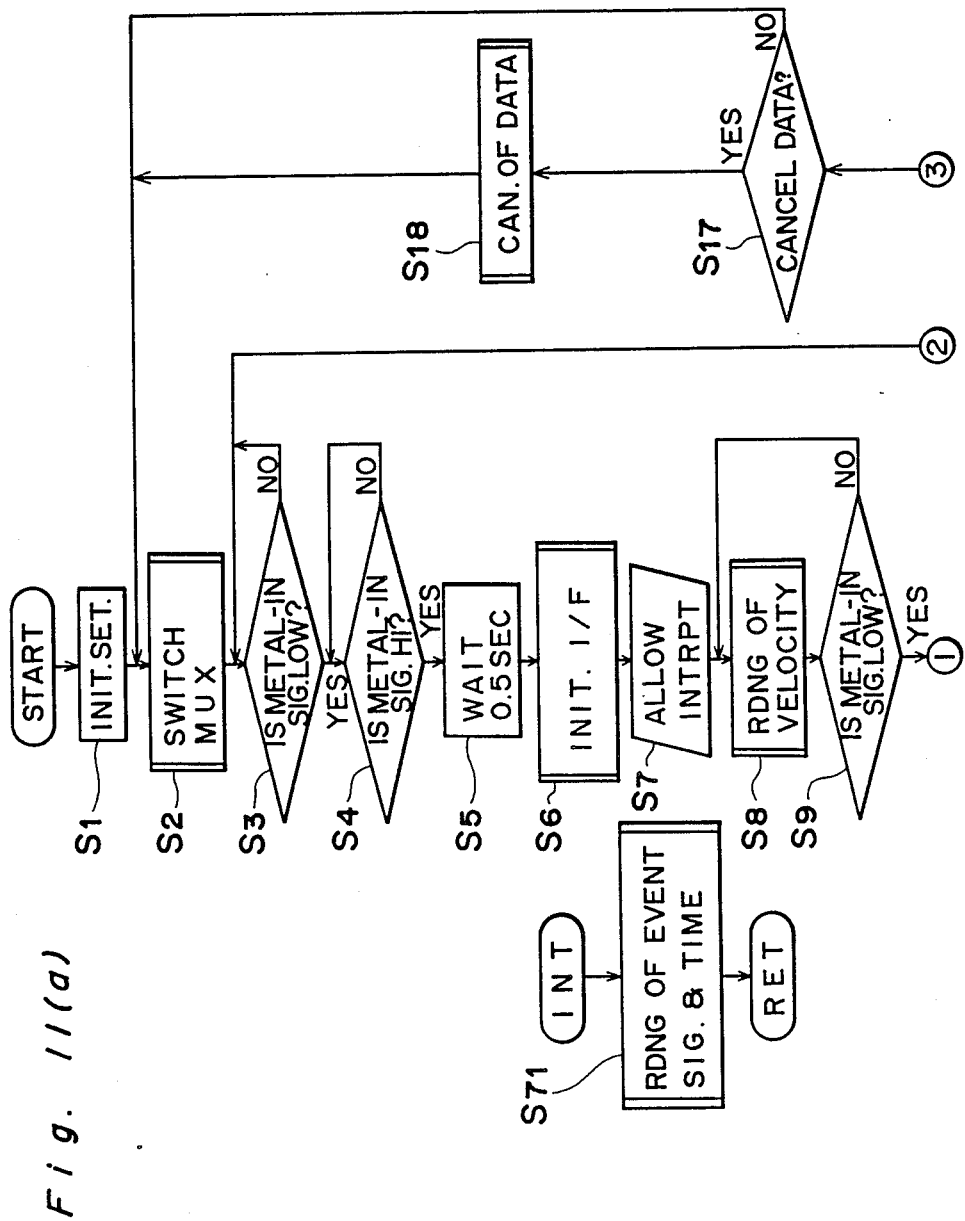
FIGS. 11(*a*) and (*b*) are flow charts describing the operation of this fourth embodiment.

In FIG. 10, 1-1, 1-2, . . . 1-n are AE sensors each of which detects AE signals from respective corresponding ball-and-roller bearings; element 22 is a multiplexer which switches AE sensors 1-1, 1-2 . . . 1-n; element 23 is a preamplifier which amplifies the AE signals from multiplexer 22; element 24 is a bandpass filter which passes, for example, AE signals from the amplifier in the range of from 100 kHz to 500 kHz; element 25 is an envelope detector which envelope-detects signals from bandpass filter 24; element 26 is a comparator which compares the envelope detected signal from envelope detector 25 with a threshold or reference value; element 27 is a central processing unit (CPU) which executes the processing shown in FIG. 11; element 28 is memory; element 29 is a rotation sensor which detects the rotation of the bearing, and element 10 is a rolling sensor which sends a rolling signal including the metal-in signal.

The method according to this embodiment is described based on FIG. 11.

First, an initial setting is made at step S1, step S2 is advanced to, multiplexer 22 is switched, and a signal from a specified AE sensor is detected.

Next, step S3 is advanced to, it is determined whether or now the metal-in signal from rolling sensor 10 becomes low, specifically, it is determined whether or not metal is being loaded. This determination is repeated if metal is currently being loaded. Specifically, the state in which metal is not loaded is first detected. If the metal-in signal is low, specifically if metal is not being loaded, step S4 is advanced to, and it is determined whether or not the metal-in signal is a high level. If the metal-in signal is not high, this determination is repeated. If the metal-in signal is high, specifically if it is determined that metal was loaded, step S5 is advanced to and there is a 0.5 sec. wait. Specifically, there is a 0.5 sec. wait to remove large AE signals after the metal-in time from the determination. Next, step S6 is advanced to, and the interface is initialized. Next, step S7 is advanced to, and interruption of signals from comparator 26 is allowed. At step S71, when comparator 26 determines that the output of the envelope detected signal is greater than the threshold or reference level, an event signal which expresses the event in which the AE signal showing bearing failure exceeds the reference level is read. Furthermore, time of event occurrence is also read at the same time. Next, step S8 is advanced to, and rotational velocity Vn of the bearing is read from rotation sensor 29. Next, step S9 is advanced to, and if the metal-in signal is low, it is determined that rolling is finished; in the case rolling is not finished, step S8 is returned to, and velocity reading occurs. If at step S9 the metal-in signal is low, specifically if the metal-out is determined, step S10 is advanced to, and interruption is prohibited. Next, step S10' is advanced to, and the data of the event signal detected at step S71 during the 0.5 sec. before the metal-out time is erased. Specifically, the data for 0.5 sec. before the metal-out time is erased to remove large AE signals before the metal-out time from failure judging. Next, step S11 is advanced to where it is determined whether or not more than two event signals were detected at step S71, specifically whether the condition in which the AE signal exceeded the reference level existed more than twice; in the case in which the event occurred twice or more, step S12 is advanced to, and the main routine is entered. Furthermore, if the event signal existed once or not even once, the later step S16 is advanced to. In the main routine of step S12, step S121 is advanced to where the rotational velocity of the bearing is corrected to a reference rotational velocity based on the bearing rotational velocity read in step S8, in other words, the period of the event signals is corrected to a period corresponding to the reference velocity. Next, step S122 is advanced to, and the the event signals are totalized for respective periods of events. Next, main routine S12 is returned to, step S13 is advanced to, and a failure determination occurs. In the case in which a failure is determined at step S13, step S14 is advanced to, a failure occurrence is displayed, and moreover the failure occurrence site is displayed. The failure occurrence site is judged to be in the inner ring, outer ring, rolling elements, or cage according to the period of the event signals. Next, step S15 is advanced to, and a warning is issued.

However, if it is determined in step S13 that a failure has not occurred, step S16 is advanced to where it is determined whether or not the processing from step S3 to S13 occurred a specified number of times for a single bearing. This specified number of times for a single bearing may be, for example, from 10 to 20 times. In this step S16, if it is determined that this series of processes has not been performed the specified number of times, step S3 is returned to, and from step S3 to S13 is repeated. In step S16, if it is determined that this series of processes has been performed the specified number of times for one bearing, step 17 is advanced to where it is determined whether or not to cancel the data, specifically, whether the measurement has been executed a prescribed number of times for all of the bearings. This prescribed number of times for one bearing may be, for example, from 50 to 100 times. If it is determined that this series of processes from step S2 to S13 has not been performed the prescribed number of times, step S2 is returned to, multiplexer 22 is switched, and the series of processes from step S2 to S13 is repeated for the next bearing. In step S17, if it is determined that the series of processes from step S3 to step S13 has been performed the prescribed number of times for all bearings, step S18 is advanced to and the data is cancelled.

In this way, bearing failures can be detected accurately and efficiently for each of a multiple number of bearings because a prescribed number of measurements are made during the rolling time excluding a given time after metal-in and a given time before metal-out to review AE signals and thereby detect bearing failures.

In the description heretofore, the case in which measurements are made for all bearings was described, but of all of the bearings, any desired number of bearings may be measured. Furthermore, if the rolling time is sufficiently long, judgement of a given period of time may also be used and not just the metal signal at step S9.

As will be clear from the above, an ball-and-roller bearing failure detection method for a rolling mill according to the present invention can accurately detect bearing failures quickly for a multiple number of bearings even if the time in which abnormality review of AE signals can be accomplished is extremely short, because whether an abnormality is generated in the AE signal is determined for a prescribed number of constant time periods for each of a multiple number of bearings.

Furthermore, an ball-and-roller bearing failure detection method for a rolling mill according to the present invention does not make erroneous judgements of bearing failure due to the AE signal during metal-in and metal-out because abnormality in AE signals is determined during the rolling time except for a given time after metal-in signal reception and a given time before metal-out signal reception.

Furthermore, in an ball-and-roller bearing failure detection method according to the present invention, the level of the AE signal due to bearing failure is high and the signal-to-noise ratio is improved because judging is accomplished with a load applied to the bearings.

(Fifth embodiment)

A fifth embodiment of the present invention is described below with reference to FIGS. 12 to 18.

A method of detecting a failure in a bearing, according to this preferred embodiment of the present invention, to be executed by a machine having an acoustic emission sensor 31 which detects acoustic emission from a bearing, a bandpass filter 33 which extracts signals in the range of from 100 kHz to 500 kHz from signals outputted of the acoustic emission sensor 31, a comparison means 36 which compares each of the signals outputted from the bandpass filter 33 with a threshold value, thereby detecting a failure in the bearing based upon a result of the comparison, is characterized by the steps of calculating, by means of a period calculation means periods during which events occur, the events being when the output signal from the bandpass filter exceeds the threshold value;

totalizing the number of events for each period calculated in the previous step;

modifying the threshold value in such a manner that the gradient of a straight line generally expressing a distribution of the number of events during each period is approximately equal to zero.

The principle of this embodiment of the present invention is herein described with reference to FIG. 13.

FIG. 13 (a) shows a detected waveform after envelope detection of AE signals; those points at which the level suddenly increases represent the AE signal emitted at failure, and the low level signal represents background noise. Also, in the case in which the threshold level is set 0.25 mV lower than the upper limit of the background noise of 1.0 mV, the relationship between the period at which the AE signal exceeds this threshold level and the number of events is shown in FIG. 13 (b). Furthermore, the number of events for the respective periods when the threshold level is set to the 1.0-mV, upper limit of the background noise, is shown in FIG. 13 (c), and the distribution of the number of events for the respective periods when the threshold level is set 0.25 mV higher than the upper limit of the background noise is shown in FIG. 13 (d). As will be understood from these FIGS. 13 (b), (c), and (d), when the threshold level is lower than the upper limit of the background noise, the distribution of the number of events is such as shown in FIG. 13 (b) in which the gradient showing the distribution of the number of events for the periods excluding AE signals emitted at the aforementioned failure times is a downward slope. Furthermore, in the case in which the threshold level is set to the upper limit of the background noise, as shown in FIG. 13 (c), when the distribution of period and number of events excluding AE signals emitted at the aforementioned failure times is linearly expressed, that linearity becomes roughly horizontal (see FIGS. 17 and 18). Furthermore, FIG. 13 (d) is similar to FIG. 13 (c). Therefore, when the threshold level is set lower than the upper limit of the background noise, it is difficult to discriminate bearing failure. Specifically, in order to discriminate background noise and the AE signal and detect the AE signal, it is sufficient to set the threshold level to the upper limit of the background noise. To set this threshold level, it is known that it is sufficient to set the threshold level so that the slope of the straight line showing the distribution of the event period and the number of events in which the AE signal exceeds the threshold level may be flat. The present invention identified this point, and was so designed.

Figure 12:
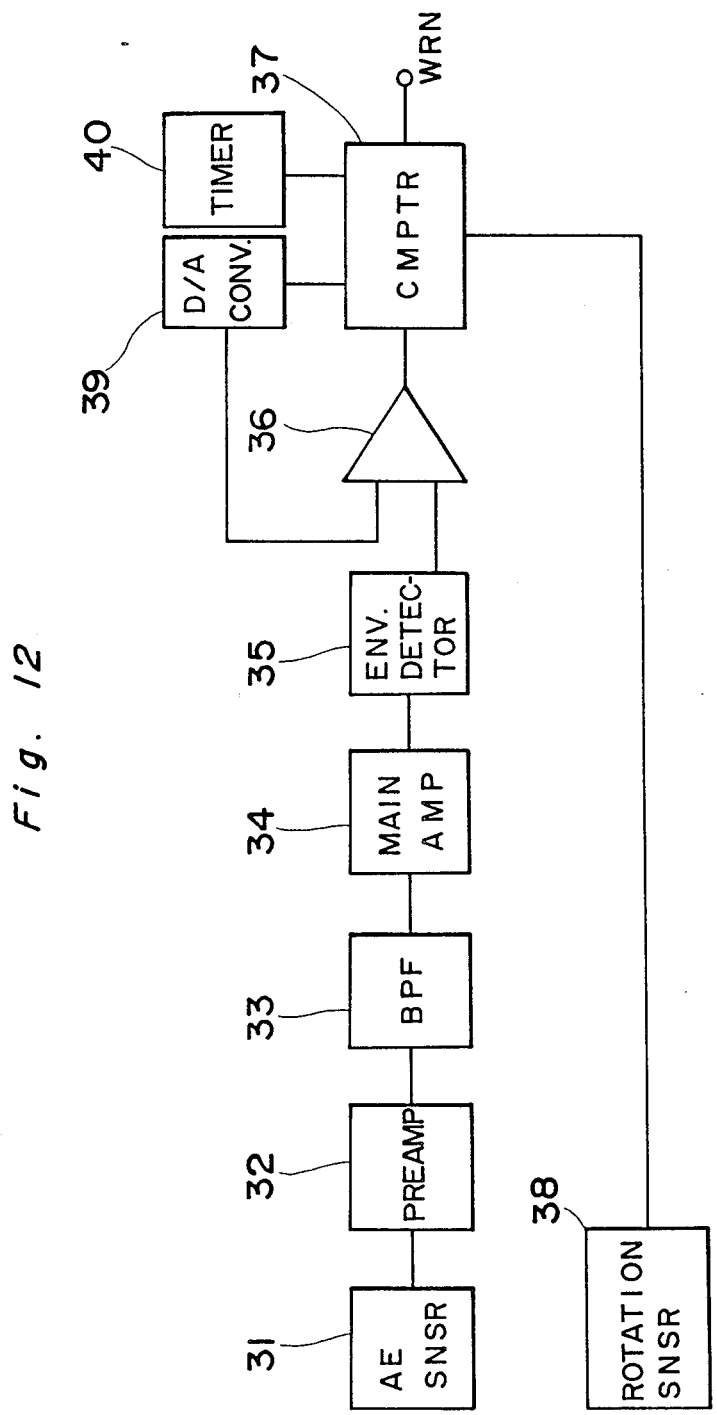
FIG. 12 is a block diagram of a fifth embodiment of the present invention.
Figure 13A:
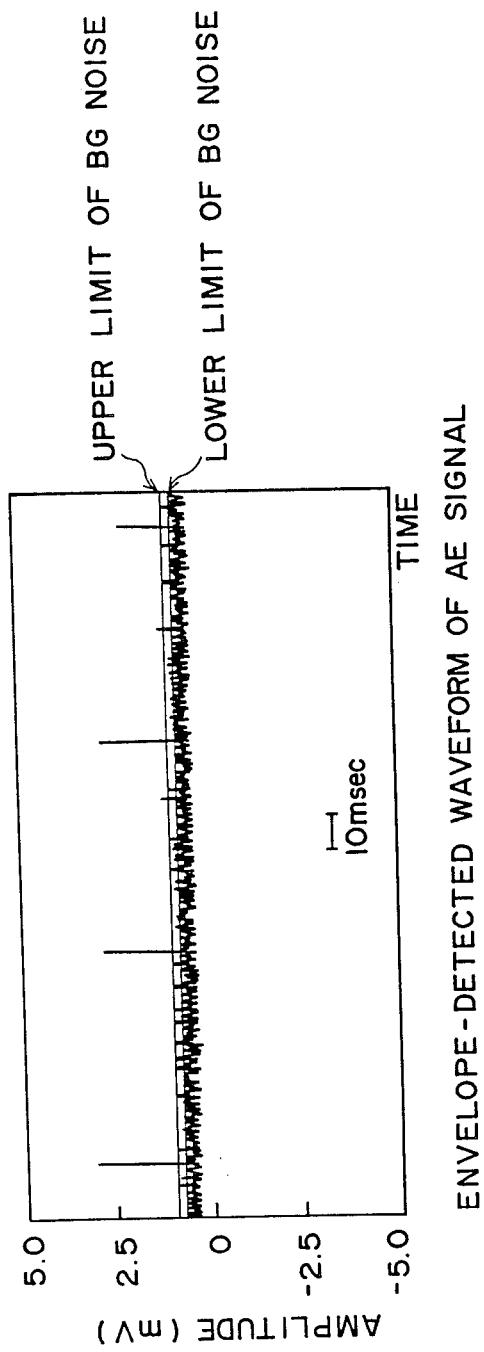
FIG. 13 (*a*) is a graph showing the envelope detected waveform of an AE signal.
Figure 13B:
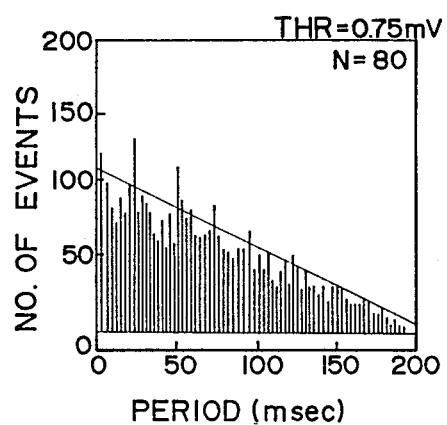
Figure 13C:
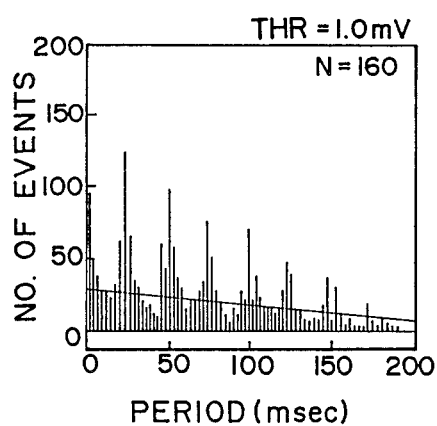
Figure 13D:
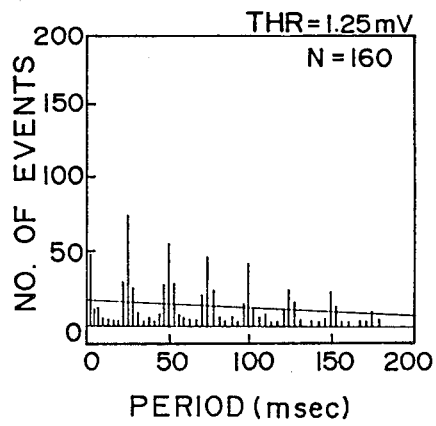

FIG. 12 is a block diagram of this embodiment. Acoustic emissions from the bearings, etc., are detected by AE sensor 31; the AE signal output from the AE sensor is amplified by preamplifier 32, and inputted to bandpass filter 33. At this bandpass filter 33, an AE signal in the range of, for example, from 100 kHz to 500 kHz is passed, and noise is removed. The AE signal from which noise has been removed is inputted from bandpass filter 33 to main amplifier 34 where it is further amplified, envelope detected by envelope detector 35, and the signal shown in FIG. 13 (a) is inputted to comparator 36. At comparator 36, a predetermined threshold value and the envelope detected AE signal are compared, and if the AE signal exceeds this threshold, a signal expressing that the AE signal exceeds the threshold level is outputted to computer 37. To computer 37 are inputted not only signals from comparator 36 but also signals from rotation sensor 38 which detects bearing rotation, and a threshold value is newly set according to the processing shown in FIG. 14. The threshold value set by the processing shown in FIG. 14 is D/A converted by D/A convertor 39, and inputted to comparator 36.

Figure 14:
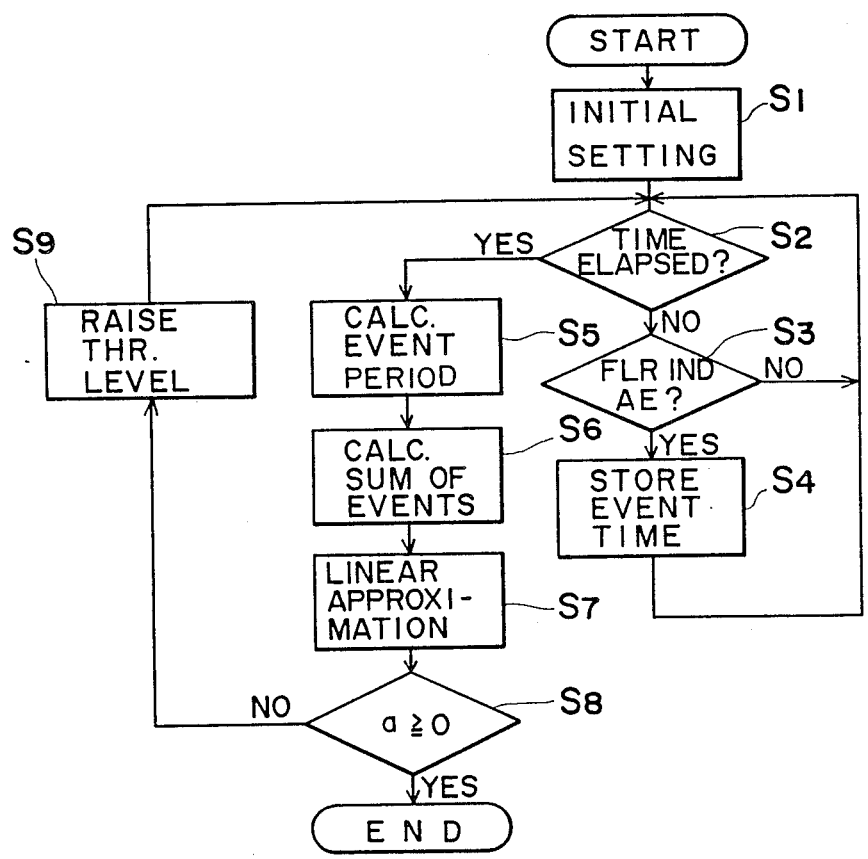
FIG. 14 is a flow chart executing a method of this embodiment.

In the aforementioned computer 37, an initial setting is first made at step S1 as shown in FIG. 14. After that, step S2 is advanced to where it is judge whether a previously defined specified time has elapsed; if this specified time has not elapsed, step S3 is advanced to where it is judged whether a pulse expressing that the AE signal has exceeded the threshold level was received from comparator 36, specifically whether acoustic emissions showing bearing failure have been emitted is judged. If it is judged that the aforementioned acoustic emissions have not been emitted at step S3, step S2 is returned to. If it is judged that the aforementioned acoustic emissions have been emitted at step S3, step S4 is advanced to and the event time of the acoustic emission is stored. The aforementioned event time is calculated by counting clocks from timer 40. After that, step S2 is returned to, and step S3 is repeated.

Figure 15:
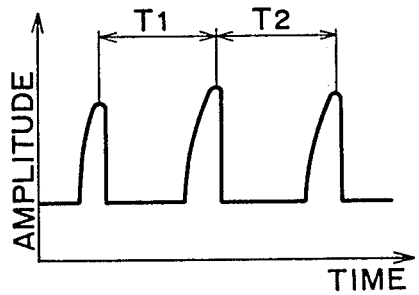
FIG. 15 is a schematic graph showing the waveform of an AE signal in which the time is plotted on the abscissa and the amplitude is plotted on the ordinate.
Figure 16:
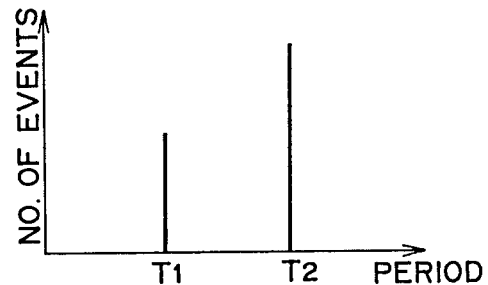
FIG. 16 is a schematic graph showing the period on the abscissa and the number of events on the ordinate.
Figure 17:
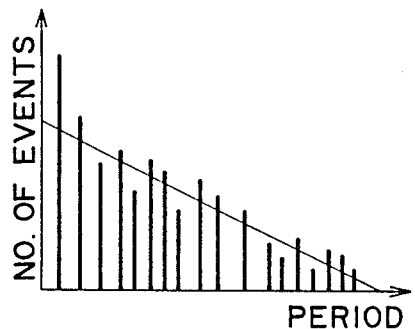
FIG. 17 and FIG. 18 are schematic graphs showing the period on the abscissa and the number of events of the AE signal on the ordinate, and which express the condition in which the distribution is generally represented by a straight line.
Figure 18:
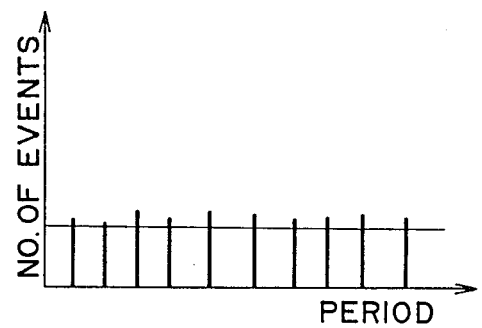

If it is judged at the aforementioned step S2 that the specified time has elapsed, step S5 is advanced to and event periods T1 and T2 of the acoustic emission as shown in FIG. 15 are calculated. Furthermore, based on a signal expressing the revolutions per unit time from rotation sensor 38, the aforementioned event periods are converted to respective periods for a reference number of revolutions of the bearing when the speed of the bearing varies with respect to the reference speed of the bearing. Specifically, the detected period of events is divided by the real number of revolutions per unit time of the bearing, and multiplied by the reference number of revolutions of the bearing to be correct to the period for the reference speed. Next, step S6 is advanced to and the number of events of acoustic emission for each event period or cycle is totalized. Specifically, as shown in FIGS. 13 (b), (c), and (d), the frequency of the number of events for each event cycle of acoustic emission is calculated. Next, step S7 is advanced to, and the distribution of the number of events of acoustic emission with respect to the period or cycle is linearly represented. Specifically, as shown in FIG. 17, when the threshold value is set lower than the upper limit of the background noise, the distribution of the number of events for each period assumes a right down-slope, and the gradient (a) of a straight line representing the distribution approximately becomes negative. Conversely, when the threshold value is set at the upper limit of the background noise, the gradient of the straight line becomes roughly flat as shown in FIG. 18. Next, step S8 is advanced to where it is judged whether the slope (a) of the straight line is zero or not as shown in FIG. 17 and FIG. 18. If the gradient (a) of the aforementioned straight line is smaller than zero, step S9 is advanced to, the threshold level is raised, and step S2 is returned to once again. However, if in step S8 it is judged that the slope of the straight line is zero or greater than zero, it is assumed that the threshold level has already been set at the upper limit of the background noise and setting of the threshold level ends.

In this way, this method enables the threshold level expressing the upper limit of the background noise to be rationally set in a manner such that the slope of a straight line expressing the distribution of the number of events of the AE signal with respect to the event period of the AE signal becomes zero, and therefore bearing failure can be accurately detected independent of worker intuition or any loss of worker actual equipment. Furthermore, automatic setting of the threshold value is possible since the threshold value expressing the background noise is set based on the event frequency distribution of the acoustic emission with respect to the event period.

In the embodiment heretofore described, the event period is compensated based on the speed of the bearing, but this compensation is not necessarily required, and this compensation may not be performed when the variations in bearing speed are slight.

As will be clear from the description heretofore, an ball-and-roller bearing failure detection method according to this embodiment of the present invention can rationally set a threshold level and accurately detect bearing failure without worker intuition or any loss of equipment which requires time or expenditure because the number of events at each event cycle or period in which the AE signal exceeds a predetermined threshold level or value is detected, a distribution of the number of events for each period is linearly represented and a threshold level is set so that the gradient of a straight line representing the above distribution may be zero.

Furthermore, an ball-and-roller bearing failure detection method according to a preferred embodiment of the present invention can automate setting of the threshold level because the threshold level is set so that the distribution of the number of events with respect to the event cycle of the AE signal is represented by a straight line and the slope of this straight line becomes flat.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An apparatus for detecting a failure in a bearing comprising:
    an acoustic emission sensor for detecting an acoustic emission from the bearing and for outputting signals indicative of power of the acoustic emission, the acoustic emission being related to the failure of the bearing;
    a bandpass filter for passing only those signals received from said sensor in the range of from 100 kHz to 500 kHz; and
    a comparison means for comparing each of the signals in the range of from 100 kHz to 500 kHz extracted by the bandpass filter with a predetermined threshold value and for outputting an event signal when the signal from the bandpass filter exceeds the threshold value;
    a period determination means for receiving the event signals from the comparison means and for determining time intervals in which the event signals occur, the time intervals being related to the portion of the bearing suffering a failure;
    a totalizing means for totaling the number of event signals for respective time intervals determined by the period determination means; and
    a judging means for judging a bearing failure when the number of events totaled by the totalizing means exceeds a predetermined threshold value.

2. An apparatus of claim 1, wherein the bandpass filter passes signals in the range of from 200 kHz to 500 kHz out of the signals received from the sensor.

3. An apparatus for detecting a failure in ball-and-roller bearings for a rolling mill comprising:
    a comparison means for comparing an acoustic emission signal indicative of power of an acoustic emission from ball-and-roller bearings with a predetermined threshold value, and for outputting an error signal which expresses a bearing failure when the power of the acoustic emission exceeds the predetermined threshold value; and
    a logic circuit for invalidating the output of the comparison means for a specified interval of time during a metal-in time when a metal sheet is loaded into the rolling mill or when the rolling of the metal sheet is started and during a metal-out time when an end of the metal sheet passes out of the mill.

4. A method of detecting a failure in a plurality of ball-and-roller bearings for a rolling mill during rolling which comprises the steps of:
    extracting, by means of a bandpass filter, only those signals in the range of from 100 kHz to 500 kHz from signals inputted from an acoustic emission sensor which detects an acoustic emission from the bearing and outputs signals corresponding thereto;
    comparing, by means of a comparison means, the signal extracted and outputted by the bandpass filter with a predetermined threshold value and generating an event signal indicative of the extracted and outputted signal being greater than the predetermined threshold value;
    storing, in a memory, an event signal, which has been generated during rolling exclusive of a given time interval occurring after reception of a metal-in signal and a given time interval occurring before reception of a metal-out signal, the metal-in signal being generated when a metal sheet is loaded into the rolling mill or when the rolling of the metal sheet is started and the metal-out signal being generated when an end of the metal sheet passes out of the mill;
    repeating the above steps of extracting, comparing, and storing a specified number of times for each of the plurality of bearings; and
    finally detecting a bearing failure based on the number of event signals stored in the memory, the acoustic emission being related to the bearing failure.

5. A method of detecting a failure in a bearing to be executed by a machine having an acoustic emission sensor which detects acoustic emission from a bearing, the acoustic emission being related to the failure of the bearing, a bandpass filter which extracts signals in the range of from 100 kHz to 500 kHz from signals outputted by the acoustic emission sensor, a comparison means which compares each of the signals outputted from the bandpass filter with a threshold value, thereby detecting a failure in the bearing based upon the comparison means detecting a signal which is greater than the threshold value, which method comprises the steps of:

determining by means of a period determination means time intervals in which the output signal from the bandpass filter exceeds the threshold value;

totaling the number of times that the output signal from the bandpass filter exceeds the threshold value for each time interval determined in the previous step;

modifying the threshold value in such a manner that the gradient of a straight line generally expressing a distribution of the number of events is approximately equal to zero.

* * * * *